United States Patent [19]

Creswell et al.

[11] Patent Number: 5,185,358
[45] Date of Patent: Feb. 9, 1993

[54] 3-HETEROATOM CONTAINING UREA AND THIOUREA ACAT INHIBITORS

[75] Inventors: Mark W. Creswell, Chelsea; Andrew D. White, Lakeland, both of Mich.

[73] Assignee: Warner-Lambert Co., Morris Plains, N.J.

[21] Appl. No.: 719,907

[22] Filed: Jun. 24, 1991

[51] Int. Cl.$^5$ .................. A61K 31/41; C07D 249/12; C07D 249/08; C07D 403/14
[52] U.S. Cl. .................. 514/383; 514/252; 514/316; 514/326; 514/384; 548/262.6; 546/187; 546/210; 544/357; 544/366
[58] Field of Search ............ 548/262.6; 546/187, 546/210; 544/357, 366; 514/383, 384, 316, 326, 252

[56] References Cited

U.S. PATENT DOCUMENTS 3,836,350  9/1974  Fawzi et al. ............... 548/262.6
3,990,879  11/1976  Soper ....................... 71/66

OTHER PUBLICATIONS

Yakugaku Zasshi 91(2), 159-65 (1971); CA 74:141216q; F. Fujikawa et al., "Studies on Chemotherapeutic Agents...".
Derwent 87-11640/17; "New 2-ureido-1,2,4--thiadiazole derivs-useful as pharmaceutical intermediates..." Oct. 15, 1985.

Primary Examiner—Patricia L. Morris
Attorney, Agent, or Firm—Ronald A. Daignault

[57] ABSTRACT

Compounds useful in treating hypercholesterolemia and atherosclerosis having the formula

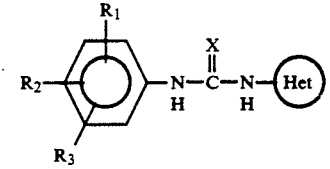

wherein X is oxygen or sulfur, Het is a monocyclic heterocyclic group having three hetero atoms selected from nitrogen, oxygen and sulfur, and $R_1$, $R_2$ and $R_3$ are hydrogen, flourine, chlorine, bromine, a straight or branched alkyl group having from 1 to 6 carbon atoms, a straight or branched alkoxy group having from 1 to 6 carbon atoms, substituted or unsubstituted benzoyl, substituted or unsubstituted benzoyl, substituted or unsubstituted phenyl, amino or substituted amino or a carboxy group.

7 Claims, No Drawings

3-HETEROATOM CONTAINING UREA AND THIOUREA ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain urea and thiourea compounds which inhibit the enzyme acyl coenzyme A:-cholesterol acyltransferase (ACAT), pharmaceutical compositions containing these compounds, and a method of treating hypercholesterolemia and atherosclerosis. This invention also describes novel intermediates useful in preparing the pharmaceutically active compounds of this invention.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposits in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides a class of compounds which have acyl-CoA:cholesterol acyltransferase (ACAT) inhibitory activity having the following structure:

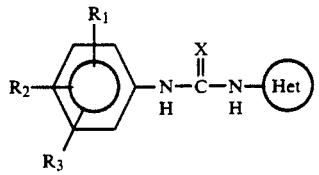

Formula I wherein X is oxygen or sulfur; wherein each of $R^1$, $R^2$, and $R^3$ is the same or different and is selected from
 hydrogen,
 fluorine,
 chlorine,
 bromine,
 a straight or branched alkyl group having from one to six carbon atoms,
 a straight or branched alkoxy group having from one to six carbon atoms,
 benzoyl which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms,
 benzyl which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms,
 phenyl which is unsubstituted or is substituted with from one to three substituents selected from fluorine, chlorine, bromine, iodine, a straight or branched alkyl group having from one to six carbon atoms, or a straight or branched alkoxy group having from one to six carbon atoms;
 —$NR_4R_5$ wherein each of $R_4$ and $R_5$ is the same or different and is hydrogen, a straight or branched alkyl group having from one to four carbon atoms, or —$NR_4R_5$ taken together form a monocyclic heterocyclic group selected from pyrrolidino, piperidino, piperazino, or piperazino substituted on the 4-position with a straight or branched alkyl group having from one to four carbon atoms;
 —$COR_6$ wherein $R_6$ is hydroxy, a straight or branched alkoxy group having from one to six carbon atoms, benzyloxy which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms, or $R_6$ is —$NR_4R_5$ wherein $R_4$ and $R_5$ have the meanings defined above;
wherein Het is selected from:

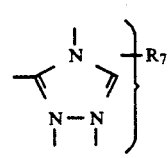

(1)

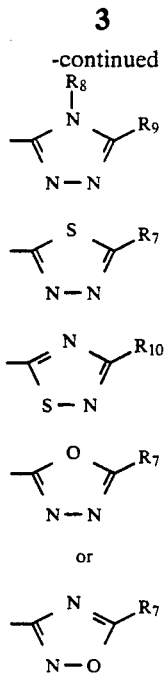

wherein R₇ is a straight or branched alkyl group having from 1 to 16 carbon atoms;
wherein R₈ is hydrogen or

wherein the alkyl moiety is straight or branched; wherein R₉ is a straight or branched alkyl group having from 1 to 16 carbon atoms or —S(O)$_p$—alkyl wherein the alkyl moiety is straight or branched and has from 1 to 16 carbon atoms and p is zero, one or two;
wherein R₁₀ is phenyl or a straight or branched alkyl group having from 1 to 16 carbon atoms; and pharmaceutically acceptable salts thereof.

DETAILED DESCRIPTION OF INVENTION

The compounds of the present invention provide a novel class of heterocyclic ureas and thioureas which are ACAT inhibitors, rendering them useful in treating hypercholesterolemia and atherosclerosis.

Illustrative examples of straight or branched alkyl groups having from 1 to 16 carbon atoms are methyl, ethyl, n propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, and 2-ethyltetradecyl.

As is apparent from Formula I above, the compounds of the present invention are arylureas and arylthioureas containing a substituted heterocyclic group selected from triazoles (1 and 2); 1,3,4-thiadiazoles (3); 1,2,4-thiadiazoles (4); 1,3,4-oxadiazoles (5); and 1,2,4-oxadiazoles (6).

Pharmaceutically acceptable salts of the compounds of Formula I are also included as a part of the present invention.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J Pharm Sci 16, 1 19 (1977).

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers on chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described by Field, F. J. and Salone, R. G., in Biochemica et Biophysica 712:557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed in IC₅₀ values; i.e., the concentration of test compound required to inhibit 50% expression of the enzyme.

TABLE 1

| Compound of Example | IC₅₀ (μM) |
|---|---|
| 1 | >5 |
| 2 | >5 |
| 4 | 4.2 |
| 6 | >5 |
| 7 | 0.14 |
| 8 | 0.11 |

TABLE 1-continued

| Compound of Example | IC$_{50}$ ($\mu$M) |
| --- | --- |
| 9 | 0.67 |
| 10 | 0.25 |
| 11 | 1.5 |
| 12 | 1.5 |
| 13 | 0.60 |
| 14 | 0.68 |
| 15 | 0.39 |
| 16 | 1.7 |
| 17 | 4.7 |
| 18 | 0.039 |
| 19 | >5 |
| 20 | 0.40 |
| 21 | 0.150 |
| 22 | 0.036 |
| 23 | 0.034 |
| 24 | >5 |
| 25 | 0.018 |
| 26 | 0.007 |
| 27 | >5 |

In one in vivo screen designated APCC, male Sprague-Dawley rats (200 to 225 g) were randomly divided into treatment groups and dosed orally at 4 PM with either vehicle (CMC/Tween) or suspensions of test compounds in vehicle. The control group received vehicle alone. Immediately after dosing, all animals received ad libitum a chow diet supplemented with peanut oil (5.5%), cholesterol (1.5%) and cholic acid (0.5%). The next day the animals were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2. The compounds were administered at 30 milligrams per kilogram of body weight.

TABLE 2

| Compound of Example | % Change (mg/dl) |
| --- | --- |
| 1 | −38 |
| 2 | −31 |
| 4 | +12 |
| 6 | −1 |
| 7 | −38 |
| 8 | −39 |
| 9 | −21 |
| 10 | −36 |
| 11 | −30 |
| 12 | −28 |
| 13 | −41 |
| 14 | −21 |
| 15 | +12 |
| 16 | −6 |
| 17 | −11 |
| 18 | −44 |
| 20 | −25 |
| 21 | −45 |
| 22 | −8 |
| 23 | −32 |
| 25 | −62 |

In therapeutic use as agents for treating hypercholesterolemia or atherosclerosis, the compounds of Formula I or pharmaceutically acceptable salts thereof are administered to the patient at dosage levels of from 250 to 300 mg per 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage form suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of Formula I are prepared by various routes as depicted in the Flow Chart hereof. In Scheme I of the Flow Chart there is depicted the synthesis of compounds of Formula I wherein Het is the group (2) wherein R$_9$ is a straight or branched alkylC$_1$-C$_{16}$. In Scheme I the aminoguanidine (a), which is commercially available, is reacted with an appropriate acid, wherein R$_a$ is a straight or branched alkylC$_1$-C$_{16}$, in the presence of N,N-dimethylaniline to give the substituted triazole amine (c). The amine (c) is reacted with an appropriate acylhalide (d) wherein alkyl is straight or branched and has from 1 to 6 carbon atoms to give the acyl amine derivative (e), which is reacted with an isocyanate or isothiocyanate (f) to give compounds of Formula I wherein Het is group (2) and further wherein R$_8$ is

—CalkylC$_{1-6}$ and R$_9$ is a straight or branched alkyl C$_1$–C$_{16}$. Compounds (g) can be hydrolyzed to the corresponding compounds of Formula I wherein R$_8$ is hydrogen. In Scheme I R$_1$, R$_2$, R$_3$, and X have the meanings defined in Formula I.

The compounds of Formula I wherein Het is group (2) wherein R$_9$ is —S(O)$_p$alkyl wherein the alkyl moiety is straight or branched and has from 1 to 16 carbon atoms are prepared as depicted in Scheme II of the Flow Chart. The commercially available thiotriazolamine (i) is alkylated using an appropriate R$_b$halo reagent wherein halo is, e.g., chlorine and R$_b$ is a straight or branched alkyl group having from 1 to 16 carbon atoms, to give compounds (j) which are acylated to give the intermediate compounds (k). The intermediates (k) are reacted with an appropriate isocyanate or isothiocyanate to give compounds of Formula I wherein Het is group (2) and wherein R$_9$ is —SalkylC$_{1-16}$ wherein the alkyl moiety is straight or branched and wherein R$_8$ is

—CalkylC$_{1-6}$.

These latter compounds are represented by (1) in Scheme II and can be hydrolyzed to the corresponding compounds (m) of Formula I wherein R$_8$ is hydrogen. The compounds of formulas (1) and (m) can be oxidized to the corresponding compounds of Formula I wherein p is one by treatment with one equivalent of m-chloroperbenzoic acid in dichloromethane at from 0° C. to 25° C. and to the corresponding compounds of Formula I wherein p is two by treatment with two equivalents of m-chloroperbenzoic acid in dichloromethane at from 0° C. to 25° C.

The compounds of Formula I wherein Het represents group (1), i.e., wherein Het is:

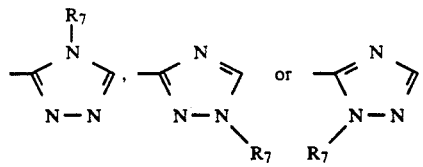

are prepared as shown in Scheme III of the Flow Chart. The triazole amine (n) is alkylated using an appropriate R$_7$ halo compound (o) to give a mixture of compounds (p), (q), and (r) which can be separated chromatographically. The alkylated triazole amine is then reacted with an isocyanate or isothiocyanate to give compounds (s), (t), and (u) which correspond to compounds of Formula I wherein Het is group (1). In Scheme III the various symbols R$_7$, R$_1$, R$_2$, R$_3$, and X have the meanings defined in Formula I.

The compounds of Formula I wherein the Het moiety is group (3) are prepared as set forth in Scheme IV of the Flow Chart. An appropriate acyl halide (v) is reacted with thiosemicarbazide (w) to give the intermediate (x) which is cyclized by treatment with an acid such as methanesulfonic acid to give the substituted thiadiazole amine (y). Reaction of (y) with an isocyanate or a isothiocyanate gives compounds of Formula I wherein Het is group (3). The acyl halides (v) are commercially available or are prepared from the corresponding acid. In Scheme IV, R$_1$, R$_2$, R$_3$, R$_7$, and X have the meanings defined in Formula I.

In Scheme V of the Flow Chart is depicted the synthesis of compounds of Formula I wherein Het is group (4), i.e., the 1,2,4-thiadiazoles. The substituted thiadiazole amines (cc) are reacted with an isocyanate or isothiocyanate (dd) to give compounds (ee) which correspond to Formula I wherein Het is group (4). The thiadiazole amine (cc) is commercially available or can be prepared from an amidine of formula (aa) by treatment with potassium thiocyanate as generally described in Adv. Heterocyl. Chem. 5:119 (1965). The amidines are commercially available or can be prepared by treatment of a nitrile, R$_{10}$CN, with ammonia in ammonium chloride under pressure. The nitriles can be obtained from the corresponding alcohols, R$_{10}$OH, by procedures well known in the art.

The preparation of compounds of Formula I wherein Het is group (5) is shown in Scheme VI of the Flow Chart. The substituted oxadiazole amine (hh) is obtained by treating a commercially available acid ester (ff) with hydrazine in a lower alcohol to give the acylhydrazide (gg) which is cyclized with cyanogen bromide by treatment with KHCO$_3$. The oxadiazole amine (hh) may also be commercially available. The acid ester (ff) can also be prepared readily from the corresponding acid. The oxadiazole amine (hh) is reacted with an appropriate isocyanate or isothiocyanate to give compounds (ii), which correspond to Formula I compounds wherein Het is group (5).

In Scheme VII of the Flow Chart is shown the synthesis of compounds of Formula I wherein Het is group (6). Hydroxyguanidine (jj) is reacted with an appropriate acid ester, R$_7$CO$_2$Me, which is commercially available or can be prepared readily from the acid, to give the oxadiazole amine (kk), which is reacted with an isocyanate or thioisocyanate to give compounds (11), which correspond to compounds of Formula I wherein Het is group (6). In Schemes VI and VII, the symbols R$_1$, R$_2$, R$_3$, R$_7$, and X have the meanings defined in Formula I.

The isocyanates and isothiocyanates depicted in the Flow Charts as

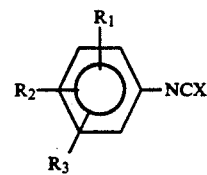

are commercially available or can be prepared by procedures well known in the art, e.g., see Jerry March, *Advanced Organic Chemistry*, Third Edition, John Wiley & Sons, 1985, p. 370.

The following specific examples further illustrate the preparation of compounds of the invention.

EXAMPLE 1

Preparation of
N-[2,6-bis(1-methylethyl)phenyl]-N'-2-acetyl-5-undecyl-2H-1,2,4-triazol-3-yl)urea Step 1—Preparation of
3-amino-5-undecyl-1H-1,2,4-triazole A slurry of aminoguanidine bicarbonate (8.0 g, 59 mmol), dodecanoic acid (11.8 g, 59 mmol), and N,N-dimethylaniline (0.1 mL, 0.8 mmol) in toluene (100 mL) was heated under reflux with the azeotropic removal of water (72 hours). The resulting slurry was cooled (25° C.) and concentrated in vacuo. The residue was partitioned between ethyl acetate (300 mL) and saturated sodium bicarbonate (300 mL). The aqueous layer was back extracted with ethyl acetate, and the combined organics were washed with brine (1×250 mL), then dried (MgSO$_4$), and concentrated in vacuo. The resulting solid was dissolved in hot chloroform and chromatographed on silica (first ethyl acetate, then 90:10 chloroform:methanol). The product containing fractions were combined and concentrated in vacuo to yield 6.9 g (49.1%) of 3-amino 5-undecyl-1H-1,2,4-triazole as an off-white powder, m.p. 128.5°–132.0° C.

Step 2—Preparation of
2-Acetyl-3-amino-5-undecyl-2H-1,2,4-triazole

Acetyl chloride (1.04 mL, 14.7 mmol) was added in one portion to a slurry of 3-amino-5-undecyl-1H-1,2,4-triazole (3.50 g, 14.7 mmol) in THF (100 mL). The resulting slurry was stirred (1 hour, 25° C.), then concentrated in vacuo. The residue was suspended in ethyl acetate (300 mL), washed with ice cold water (2×100 mL), washed with ice cold brine (1×100 mL), then dried (MgSO$_4$) and concentrated to yield 3.66 g (89.3%) of 2-acetyl-3-amino-5-undecyl-2H-1,2,4-triazole as a waxy solid.
Analysis for $C_{15}H_{28}N_4O$:
Calcd: C, 64.25; H, 10.06; N, 20.07.
Found: C, 64.08; H, 9.77; N, 19.57.

Step 3—Preparation of
N-[2,6-bis(1-methylethyl)phenyl]-N'-(2-acetyl-5-undecyl-2H-1,2,4-triazol-3-yl)urea A slurry of 1-acetyl-5-amino-3-undecyl-1,2,4-triazole (3.56 g, 12.7 mmol) was warmed until homogeneous. 2,6-Diisopropylphenyl isocyanate (2.71 mL, 12.7 mmol) was added and the resulting solution was heated under reflux for 15 hours. The resulting solution was cooled (20° C.) and the precipitate was removed by filtration. The filtrate was concentrated in vacuo and the resulting oil was chromatographed on silica (85:15 hexane:ethyl acetate) to yield 4.07 g (66.3%) of the title compound as a light yellow oil.
Analysis for $C_{28}H_{45}N_5O_2$:
Calcd: C, 69.53; H, 9.38; N, 14.48.
Found: C, 69.51; H, 9.49; N, 14.38.

EXAMPLE 2

Preparation of
N-[2,6-bis(1-methylethyl)phenyl]-N'-(5-undecyl-1H-1,2,4-triazol-3-yl)urea A solution of N-[2,6-bis(1-methylethyl)phenyl)-N'-(2-acetyl-5-undecyl-2N-1,2,4-triazol-3-yl)urea (2.17 g, 4.49 mmol) in methanol (50 mL) was stirred for 24 hours at 25° C. The resulting slurry was cooled (−20° C.), then the precipitate collected by filtration, washed with cold methanol, and dried in a vacuum oven (16 hours, 40° C.) to yield 1.78 g (89.9%) of the title compound as a white powder; m.p. 168°–170° C. (resolidified and decomposed at 210° C.).
Analysis for $C_{26}H_{43}N_5O$:
Calcd: C, 70.71; H, 9.81; N, 15.86.
Found: C, 70.77; H, 9.89; N, 15.98.

EXAMPLE 3

Preparation of
N-[2,6-bis(1-methylethyl)phenyl]-N'(2-acetyl-5-dodecyl-2H-1,2,4-triazol-3-yl)urea Employing the general method of Example 1, but using tridecanoic acid instead of dodecanoic acid in Step 1, the title compound was prepared.
Analysis for $C_{29}H_{47}N_5O_2$:
Calcd: C, 69.98; H, 9.52; N, 14.07.
Found: C, 69.74; H, 9.46; N, 13.83.

EXAMPLE 4

Preparation of
N-[2,6-bis(1-methylethyl)phenyl]-N'(5-dodecyl-1H-1,2,4-triazol-3-yl)urea Employing the general method of Example 2 but using N-[2,6-bis(1-methylethyl)phenyl]-N'-(2-acetyl-5-dodecyl-2H-1,2,4-triazol-3-yl)urea instead of N-[2,6-bis(1-methylethyl)phenyl]-N'-(2-acetyl-5-undecyl-2H-1,2,4-triazol-3-yl)urea, the title compound was prepared; m.p. 154°–164° C.

EXAMPLE 5

Preparation of
N-[2,6-bis(1-methylethyl)phenyl]-N'-(2-acetyl-5-tetradecyl-2H-1,2,4-triazol-3-yl)urea Employing the general method of Example 1 but using pentadecanoic acid instead of dodecanoic acid in Step 1, the title compound was prepared.
Analysis for $C_{31}H_{51}N_5O_2$:
Calcd: C, 70.82; H, 9.78; N, 13.32.
Found: C, 70.72; H, 9.82; N, 13.16.

EXAMPLE 6

Preparation of
N-[2,6-bis(1-methylethyl)phenyl]-N'(5-tetradecyl)-1H-1,2,4-triazol-3-yl)urea Employing the general method of Example 2, but using N-[2,6-bis(1-methylethyl)phenyl]-N'-(2-acetyl-5-tetradecyl-2H-1,2,4-triazol-3-yl)urea instead of N-[2,6-bis(1-methylethyl)phenyl]-N'-(2-acetyl-5-undecyl-2H-1,2,4-triazol-3-yl)urea, the title compound was prepared; mp 211° C. decomposes.
Analysis for $C_{29}H_{49}N_5O$:
Calcd: C, 72.01; H, 10.21; N, 14.48.
Found C, 72.08; H, 10.29; N, 14.34.

EXAMPLE 7

Preparation of
N-[2,6-bis(1-methylethyl)phenyl)-N'(2-undecyl-2H-1,2,4-triazol-3-yl)urea Step 1—Preparation of
3-amino-2-undecyl-1,2,4-triazole;
3-amino1-undecyl-1,2,4-triazole; and
3-amino4-undecyl-1,2,4-triazole A methanol solution of sodium methoxide was generated by dissolving sodium (2.06 g, 89.6 mmol) in methanol (300 mL). 3-Amino-1,2,4-triazole (7.5 g, 89.6 mmol) was added and the resulting solution was stirred (10 minutes, 25° C.). Undecylbromide (20.0 mL, 89.6 mmol) was then added and the resulting solution was heated under reflux for 24 hours. The resulting solution was cooled (25° C.) and concentrated in vacuo. The residue was taken up in ethyl acetate (450 mL), washed with brine (2×150 mL), then dried (MgSO$_4$) and concentrated in vacuo. The resulting solid was dissolved in a minimal amount of chloroform and chromatographed on silica (98:2 chloroform:methanol) to yield 3.0 g (14.0%) of 3-amino-2-undecyl-1,2,4 -triazol (analysis for $C_{13}H_{26}N_4$: Calcd: C, 65.50; H, 10.99; N, 23.50; Found: C, 65.49; H, 10.98; N, 23.88), 4.0 g (18.7%) of 3-amino-1-undecyl-1,2,4-triazole (analysis for $C_{13}H_{26}N_4$: Calcd: C, 65.50; H, 10.99; N, 23.50; Found: C, 65.42; H, 10.93; N, 23.48), and 0.9 g (4.2%) of 3-amino-4-undecyl-1,2,4-triazole (analysis for $C_{13}H_{26}N_4$: Calcd: C, 65.50; H, 10.99; N, 23.50; Found: C, 65.20; H, 10.92; N, 23.52).

Step 2—Preparation of
N-[2,6-bis(1-methylethyl)phenyl]-N'-(2-undecyl-2H-1,2,4-triazol-3-yl)urea A solution of 3-amino-2-undecyl-1,2,4-triazole (3.0 g, 12.6 mmol) and 2,6-diisopropylphenyl isocyanate (3.9 mL, 19.2 mmol) in THF (100 mL) was heated under reflux (40 hours). The resulting solution was cooled (25° C.) and concentrated in vacuo. The resulting oil was triturated with hexane and the resulting solid was collected by filtration and recrystallized from hot hexane to yield 2.1 g (37.8%) of the title compound as a white solid; mp 146.5°–147.5° C.

EXAMPLE 8

Preparation of
N-[2,6-bis(1-methylethyl)phenyl]-N-(1-undecyl-1,2,4-triazol-3-yl)urea Using the procedure of Step 2 of Example 7, but using 3-amino-1-undecyl-1,2,4-triazole instead of 3-amino-1-undecyl-1,2,4-triazole, the title compound was prepared.
Analysis for $C_{26}H_{43}N_5O$:
Calcd: C, 70.71; H, 9.81; N, 15.86.
Found: C, 70.69; H, 10.07; N, 16.11.

EXAMPLE 9

Preparation of
N-[2,6-bis(1-methylethyl)phenyl]-N'(4-undecyl-1,2,4-triazol-3-yl)urea Using the procedure of Step 2 of Example 7, but using 3-amino-4-undecyl-1,2,4-triazole instead of 3-amino-2-undecyl-1,2,4-triazole, the title compound was prepared. $^1$H NMR (250 MHz, DMSO) δ 9.57 (s, 1H), 9.31 (s, 1H), 8.39 (s, 1H), 7.20 (m, 3H), 3.92 (t, 2H), 3.33 (p, 2H), 1.67 (m, 2H), 1.20 (m, 28H), 0.85 (t, 3H).

EXAMPLE 10

Preparation of
N-[2,6-bis(1-methylethyl)phenyl]-N'-(2-dodecyl-1H-1,2,4-triazol-5-yl)urea Employing the general method of Example 7, but using dodecylbromide instead of undecylbromide in Step 1, the title compound was prepared; mp 128°–140° C.

EXAMPLE 11

Preparation of
N-[2,6-bis(1-methylethyl)phenyl]-N'-(1-dodecyl-1H-1,2,4-triazol-3-yl)urea Employing the general method of Example 7, but using dodecyl bromide instead of undecyl bromide in Step 1, the title compound was prepared.
Analysis for $C_{27}H_{45}N_5O$:
Calcd: C, 71.17; H, 9.95; N, 15.37.
Found C, 71.34; H, 10.18; N, 15.41.

EXAMPLE 12

Preparation of
N-[2,6-bis(1-methylethyl)phenyl]-N'-(4-dodecyl-4H-1,2,4-triazol-3-yl)urea Employing the general method of Example 7, but using dodecylbromide instead of undecylbromide in Step 1, the title compound was prepared.
Analysis for $C_{27}H_{45}N_5O$:
Calcd: C, 71.17; H, 9.95; N, 15.37.
Found: C, 71.34; H, 10.24; N, 14.79.

EXAMPLE 13

Step 1

12-Bromododecane (11.7 g, 0.05 mol) was added to a slurry of 3 amino 5 mercapto-1,2,4-triazole (5.0 g, 0.043 mol) and triethyl amine (4.7 g, 0.05 mol) in acetonitrile (150 mL). The mixture was allowed to reflux for 4 hours, cooled, and the precipitate filtered and recrystallized from acetonitrile to give 9.55 g of 2 dodecylthio-5-amino-1,2,4-triazole as a white solid, m.p. 93°–99° C.
Calcd: C, 59.11; H, 9.92; N, 19.70; S, 11.27.
Found: C, 59.41; H, 10.20; N, 19.40; S, 11.34.

Step 2

Acetyl chloride (0.61 g, 0.007 mol) was added to a cooled (0° C.) solution of the product of Step 1 (2.0 g, 0.007 mol) and triethyl amine (0.80 g, 0.008 mol) in THF (50 mL). The mixture was stirred for 30 minutes at 0° C., poured into ethyl acetate, and washed with ice cold water and brine, dried over Na$_2$SO$_4$, filtered, and concentrated in vacuo. The solid obtained was washed with acetonitrile and dried in vaco to give 1-acetyl-2-dodecylthio-5-aminotriazole as a white solid (1.5 g), m.p. 92°–97° C.

Step 3—Preparation of
4-acetyl-N-[[[2,6-bis(1-methylethyl)phenyl]amino]carbonyl]-5-(dodecylthio)-4H-1,2,4-triazol-3-amine 2,6-Diisopropylphenylisocyanate (2.1 g, 0.01 mol) was added to a solution of 4-acetyl-5 -dodecylthio-3-aminotriazole (2.8 g, 0.09 mol) in THF (80 mL) and the mixture refluxed for 24 hours. The solution was concentrated in vacuo and the residue triturated with acetonitrile. The mixture obtained was filtered and the filtrate concentrated in vacuo and chromatographed on silica gel, eluting with 5% to 8% ethyl acetate in hexanes to give 1.1 g of the title compound as an oil.
Calcd: C, 65.75; H, 8.94; N, 13.22; S, 6.05.
Found: C, 65.70; H, 8.65; N, 13.20; S, 6.00.

EXAMPLE 14

4-Acetyl-N-[[[2,6-bis(1-methylethyl)phenyl]amino]carbonyl]-5-(tridecylthio)-4H-1,2,4-triazol-3-amine When in the procedure of Example 13 an appropriate amount of 13-bromotridecane was substituted for 12-bromododecane and the general procedure of Steps 1, 2, and 3 of Example 13 were followed, the title compound was obtained as an oil.

Calcd: C, 66.26; H, 9.08; N, 12.88; S, 5.88.
Found: C, 66.30; H, 9.28; N, 12.70; S, 5.86.

EXAMPLE 15

N-[[[2,6-Bis(1-methylethyl)phenyl]amino]carbonyl]-5-(tridecylthio)-4H-1,2,4-triazol-3-amine The urea of Example 14 (4.4 g, 0.0081 mol) was stirred in methanol (100 mL) at room temperature for 2 hours, the solution was then allowed to stand overnight. The solid obtained was filtered and dried in vacuo to give a white solid (2.57 g), m.p. 131°-135° C.

Calcd: C, 67.02; H, 99.44; N, 13.96.
Found: C, 66.91; H, 9.35; N, 13.66.

EXAMPLE 16

N-[2,6-Bis(1-methylethyl)phenyl]-N'-[5-(tridecylsulfinyl)-1H-1,2,4-triazol-3-yl]urea m-Chloroperbenzoic acid (0.26 g, 1.49 mmol) was added to a cooled (0° C.) solution of the compound of Example 15 in dichloromethane (25 mL). The solution was allowed to warm to room temperature and stirred for 4 hours. The mixture was diluted with $CH_2Cl_2$ (100 mL) and washed sequentially with $NaHSO_3$, water, $NaHCO_3$, and brine, dried over $Na_2SO_4$, concentrated, and triturated with hexane to give a white solid which was filtered and dried in vacuo to yield 0.42 g; m.p. 178°-181° C.

EXAMPLE 17

N-[2,6-Bis(1-methylethyl)phenyl]-N'-5-tridecylsulfonyl)-1H-1,2,4-triazol-3-yl]urea m-Chloroperbenzoic acid (0.52 g, 3.0 mmol) was added to a cooled (0° C.) suspension of the compound of Example 16 (0.5 g, 1 mmol) in dichloromethane (25 mL). The mixture was allowed to warm to room temperature and stirred for 18 hours. The reaction was diluted with $CH_2Cl_2$ (100 mL) and washed sequentially with $NaHSO_3$, water, $NaHCO_3$, dried with $Na_2SO_4$, filtered, concentrated, and recrystallized from acetonitrile to give 0.36 g of a solid, m.p. 136°-138° C.

EXAMPLE 18

Step 1—Preparation of Dodecanoic acid 2-(aminothioxomethyl)hydrazide

Lauroyl chloride (12.9 g, 0.06 mol) in THF (70 mL) was added dropwise to a vigorously stirred suspension of thiosemicarbazide (10.9 g, 0.12 mol) in THF (300 mL) at 0° C. After the addition was complete, the mixture was allowed to warm to room temperature and stirred for 24 hours. The mixture was concentrated in vacuo to one-quarter of the original volume and filtered through a silica pad, eluting with ethyl acetate (500 mL). The filtrate was concentrated to 250 mL, filtered, and the residue washed with ethyl acetate and dried in vacuo to give 12.0 g of a white solid.

Calcd: C, 57.10; H, 9.95; N, 15.37; S, 11.73.
Found: C, 56.71; H, 9.97; N, 15.22; S, 11.78.

Step 2—Preparation of 5-undecyl-1,3,4-thiadiazol-2-amine

Methanesulfonic acid (6.26 g, 0.065 mol) was added in one portion to a slurry of the compound prepared in Step 1 above (11.9 g, 0.044 mol) in toluene (300 mL) at 0° C. After 5 minutes, the mixture was heated to reflux for 18 hours, allowed to cool to 0° C., filtered, and the residue washed with cold toluene (50 mL at 5° C). The solid was dried in vacuo, suspended in water (200 mL), and made basic with ammonium hydroxide (0.1M) while stirring vigorously. The resulting solid was filtered, washed with water, dried in vacuo to give 7.2 g of a white solid.

Calcd: C, 61.13; H, 9.87; N, 16.45; S, 12.55.
Found: C, 60.93; H, 9.87; N, 16.80; S, 12.98.

Step 3—Preparation of N-[2,6-bis(1-methylethyl)phenyl]-N'-(5-undecyl-1,3,4-thiadiazol-2-yl)urea 2,6-Diisopropylphenylisocyanate (3.85 g, 0.019 mol) was added to a solution of the compound from Step 2 above (4.4 g, 0.017 mol) in acetonitrile (150 mL). The mixture was refluxed for 1 hour and then allowed to stand at room temperature overnight, concentrated to ¾ volume, and filtered. The residue obtained was washed with acetonitrile (50 mL) and hexanes (200 mL) to give 5.9 g of a white solid, m.p. 111°-113° C.

Calcd: C, 68.08; H, 9.23; N, 12.21; S, 6.99.
Found C, 67.64; H, 9.17; N, 12.25; S, 6.97.

When in the procedure of Example 18, Step 1, an appropriate amount of the acyl chloride listed below was substituted for lauroyl chloride and the general procedure of Steps 1, 2, and 3 of Example 18 were followed, the respective compounds listed below were obtained:

| Example Number | Acylchloride | Compound |
| --- | --- | --- |
| 19 | acetyl chloride | N-[2,6-bis(1-methylethyl)phenyl]-N'-(5-methyl-1,3,4-thiadiazol-2-yl)urea, m.p. 295-297° C., dec. |
| 20 | octanoyl chloride | N-[2,6-bis(1-methylethyl)phenyl]-N'-(5-heptyl-1,3,4-thiadiazol-2-yl)urea, m.p. 102-110° C. |
| 21 | decanoyl chloride | N-[2,6-bis(1-methylethyl)phenyl]-N'-(5-nonyl-1,3,4-thiadiazol-2-yl)urea, m.p. 94-98° C. |
| 22 | tetradecanoyl chloride | N-[2,6-bis(1-methylethyl)phenyl]-N'-(5-tridecyl-1,3,4-thiadiazol-2-yl)urea, m.p. 85-91° C. |
| 23 | tridecanoyl chloride | N-[2,6-bis(1-methylethyl)phenyl]-N'-(5-dodecyl-1,3,4-thiadiazol-2-yl)urea, m.p. 93-105° C. |

EXAMPLE 24

N-[2,6-Bis(1-methylethyl)phenyl]-N'-(3-phenyl-1,2,4-thiadiazol-5-yl)urea 2,6-Diisopropylphenylisocyanate (1.9 g, 9.4 mmol) was added to a refluxing solution of 5-amino-3-phenyl- 1,2,4-thiadiazole (1.5 g, 8.5 mmol) in acetonitrile (60 mL). The mixture was refluxed for 18 hours, allowed to cool, filtered, and the filtrate concentrated, taken up in ethyl acetate (150 mL), and washed with water (3×50 mL). The organics were dried over Na$_2$SO$_4$, filtered, concentrated, and the resulting solid washed with hexane and recrystallized from acetonitrile to give a white solid (1.50 g, 46%), m.p. 180°–183° C.

EXAMPLE 25

Step 1—Preparation of tetradecanoic acid hydrazide

Hydrazine (1.9 mL, 0.058 mol) was added to a solution of methyl tetradecanoate (13.96 g, 0.058 mol) in methanol (300 mL) and the solution refluxed for 3 days. The mixture was allowed to cool and filtered to yield 6.17 g of a crystalline solid, m.p. 107°–111° C.

Step 2—Preparation of 2-amino-5-tridecyl-1,3,4-oxadiazole

Cyanogen bromide (2.9 g, 0.027 mol) was added to a mixture of the compound prepared in Step 1 above (6.1 g, 0.025) and KHCO$_3$ (2.8 g, 0.028 mol) in dioxane/water (1:1, 50 mL) at room temperature. The mixture was refluxed for 1 hour, allowed to cool, filtered, washed with dioxane/water (1:1, 20 mL), then water (50 mL), and dried in vacuo. The solid was recrystallized from chloroform to yield 4.16 g, m.p. 147°–150° C.

Calcd: C, 67.37; H, 10.92; N, 15.71.
Found: C, 67.37; H, 11.03; N, 15.69.

Step 3—Preparation of N-[2,6-bis(1-methylethyl)phenyl]-N'-(5-tridecyl-1,3,4-oxadiazol-2-yl)urea Triethylamine (1.67 g, 0.017 mol) was added to a solution of the compound prepared in Step 2 above (4.0 g, 0.015 mol) in acetonitrile (200 mL) and the mixture refluxed for 30 minutes or until solution becomes homogeneous. 2,6-Diisopropylphenyl isocyanate (3.71 g, 0.018 mol) was then added and reflux continued for 18 hours. The mixture was allowed to cool, concentrated, diluted with water (20 mL), filtered, and the solid columned on silica gel, eluting with 20% ethyl acetate in hexanes (loaded in chloroform) to give 0.54 g of a solid; m.p 114°–116.5° C.

EXAMPLE 26

Step 1—Preparation of 3-amino-5-tridecyl-1,2,4-oxadiazole

Sodium metal (1.6 g, 0.068 mol) was added to 4 Å molecular sieves (12 g) and ethanol (200 mL) under nitrogen. The mixture was stirred for 15 minutes, then hydroxyguanidine sulfate (9.32 g, 0.035 mol) added and the mixture stirred for 30 minutes. Methyltetradecanoate (1.43 g, 0.006 mol) was then added and the mixture refluxed for 1.5 hours, allowed to cool, filtered, and concentrated. The concentrate was partitioned between CH$_2$Cl$_2$ and water. The organic layer was washed with water and brine, dried with Na$_2$SO$_4$, filtered, concentrated, and triturated with hexane. The resulting solid was filtered, washed with hexane, and dried in vacuo to yield 0.23 g, m.p. 90°–91° C.

Step 2—Preparation of N-[2,6-bis(1-methylethyl)phenyl]-N'-[5-tridecyl-1,2,4-oxadiazol-3-yl]urea 2,6-Diisopropylphenylisocyanate (0.29 g, 0.0013 mol) was added to a refluxing solution of the compound prepared in Step 1above (0.18 g, 0.65 mmol) in acetonitrile (20 mL) and the mixture refluxed overnight. The solution was allowed to cool to room temperature, concentrated, triturated with acetonitrile to yield a solid which was recrystallized from acetonitrile to yield 0.15 g, m.p. 99°–101°.

Calcd: C, 71.45; H, 9.85; N, 11.90.
Found: C, 70.43; H, 9.84; N, 12.05.

EXAMPLE 27

N-[2,6-Bis(1-methylethyl)phenyl]amino]carbonyl]-5-(methylthio)-4H-1,2,4-triazol-3-amine When in the procedure of Example 13, Step 1, an appropriate amount of methyliodide is substituted for 12-bromododecane and the general procedure of Steps 1, 2, and 3 of Example 13 are followed, 4-acetyl-N-[[[2,6-bis(1-methylethyl)phenyl]amino]carbonyl]-5-(1-methylthio)-4H-1,2,4-triazol-3-amine is obtained. When this 4-acetyl derivative is substituted for the compound of Example 14 in the procedure of Example 15, the title compound is obtained, m.p. 192°–197° C. (dec.).

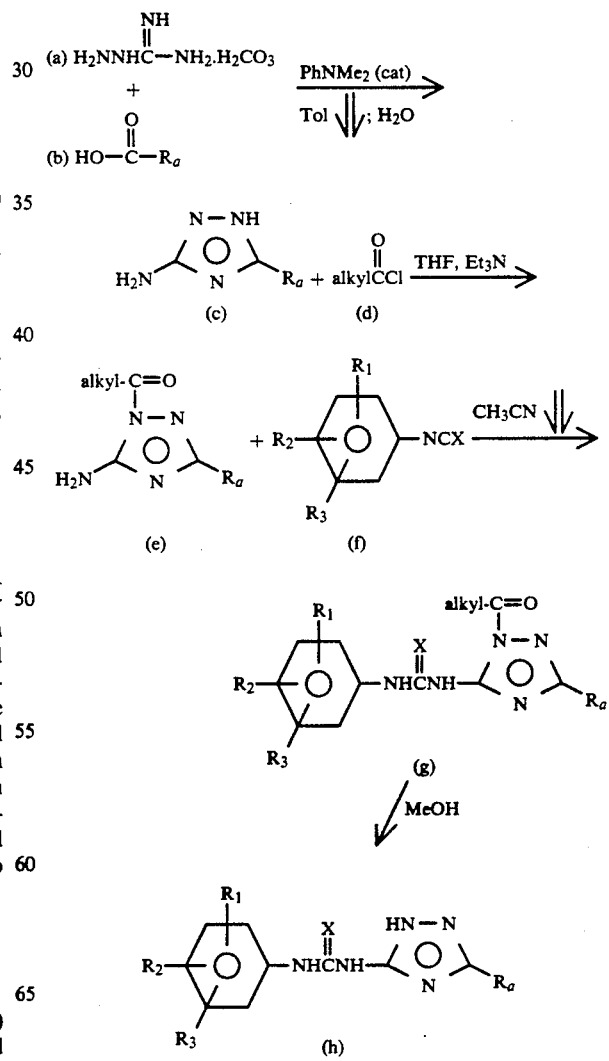

Scheme I

Scheme II
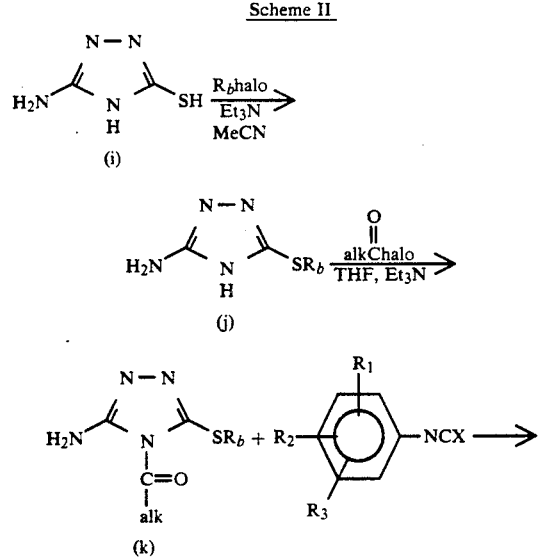
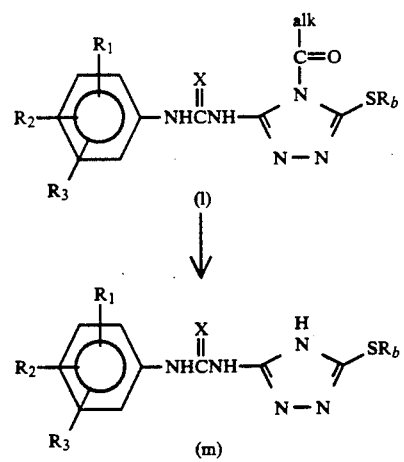
Scheme III
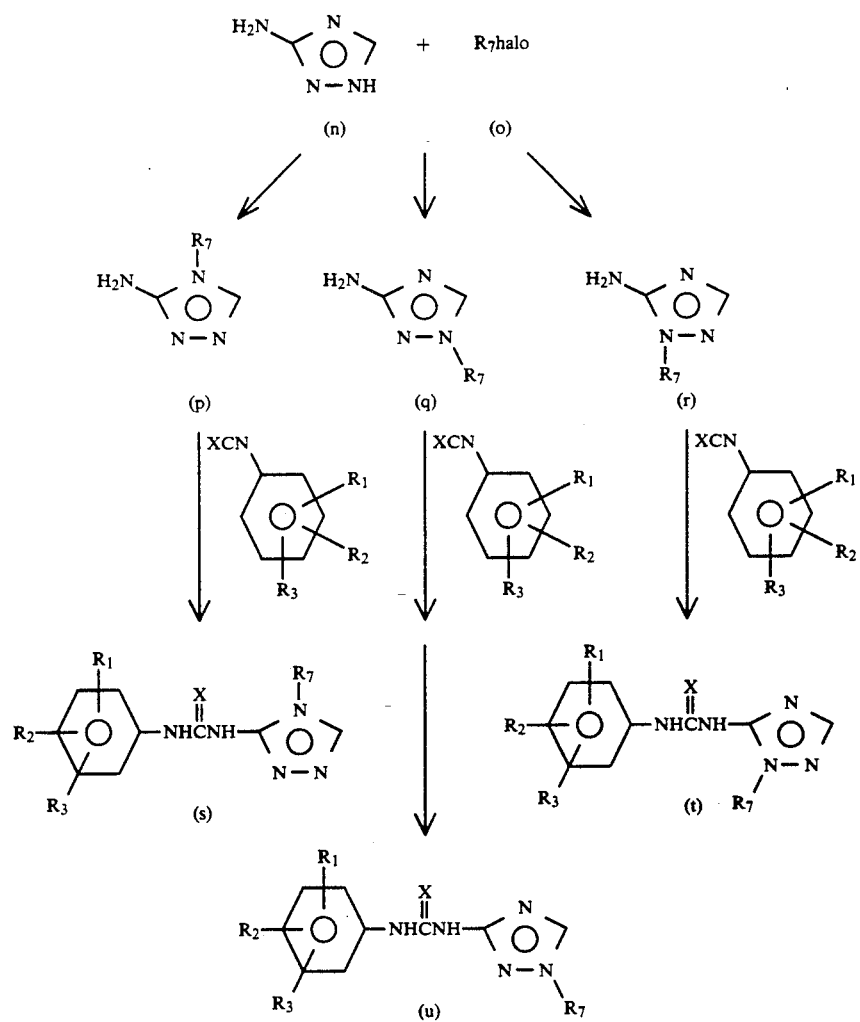

Scheme IV
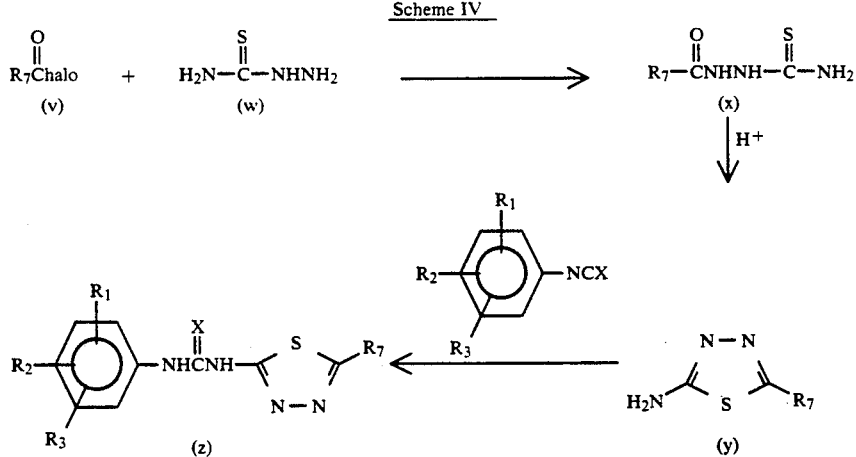
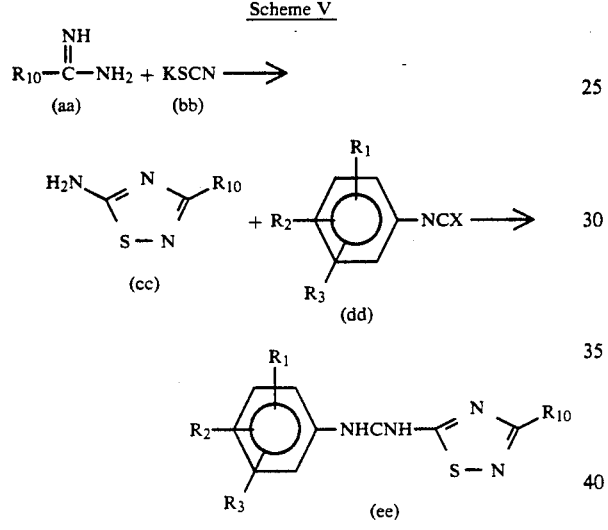
Scheme V
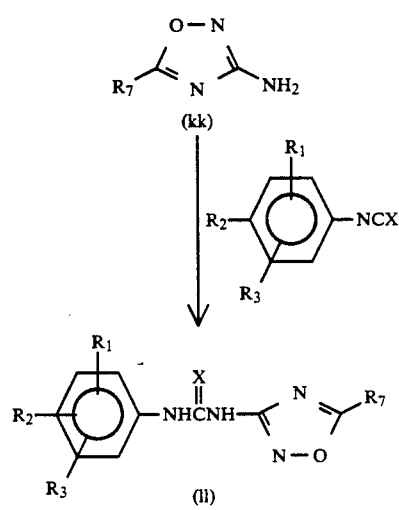
-continued
Scheme VII
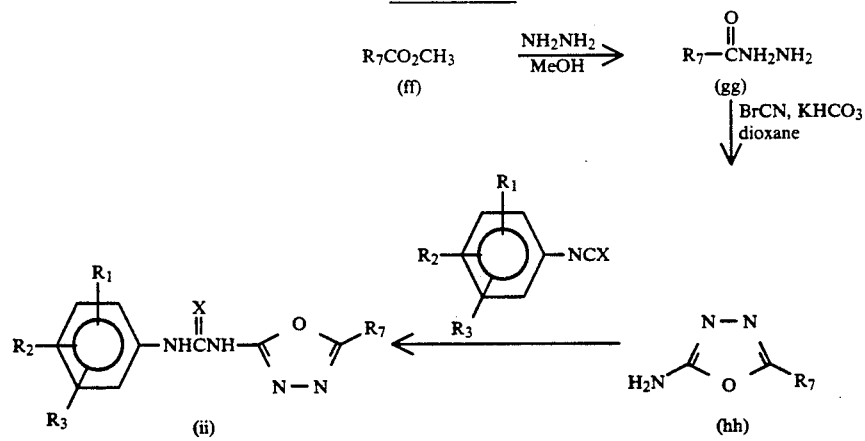
Scheme VI
Scheme VII
We claim:
1. A compound of the formula

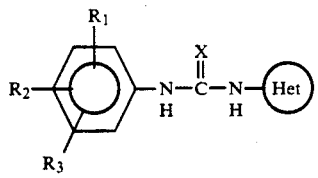

wherein X is oxygen or sulfur; wherein each of $R^1$, $R^2$, and $R^3$ is the same or different and is selected from
hydrogen,
fluorine,
chlorine,
bromine,
a straight or branched alkyl group having from one to six carbon atoms,
a straight or branched alkoxy group having from one to six carbon atoms,
benzoyl which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms,
benzyl which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms,
phenyl which is unsubstituted or is substituted with from one to three substituents selected from fluorine, chlorine, bromine, iodine, a straight or branched alkyl group having from one to six carbon atoms, or a straight or branched alkoxy group having from one to six carbon atoms;
—$NR_4R_5$ wherein each of $R_4$ and $R_5$ is the same or different and is hydrogen, a straight or branched alkyl group having from one to four carbon atoms, or —$NR_4R_5$ taken together form a monocyclic heterocyclic group selected from pyrrolidino, piperidino, piperazino, or piperazino substituted on the 4-position with a straight or branched alkyl group having from one to four carbon atoms;
—$COR_6$ wherein $R_6$ is hydroxy, a straight or branched alkoxy group having from one to six carbon atoms, benzyloxy which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms, or $R_6$ is —$NR_4R_5$ wherein $R_4$ and $R_5$ have the meanings defined above;
wherein Het is selected from:

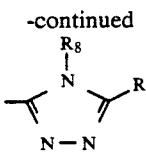

or

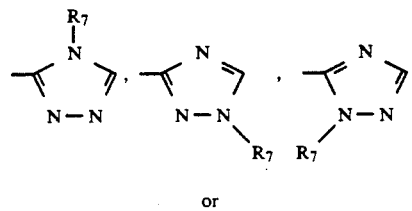

wherein $R_7$ is a straight or branched alkyl group having from 1 to 16 carbon atoms;
wherein $R_8$ is hydrogen or

wherein the alkyl moiety is straight or branched;
wherein $R_9$ is a straight or branched alkyl group having from 1 to 16 carbon atoms or —$S(O)_p$-alkyl wherein the alkyl moiety is straight or branched and has from 1 to 16 carbon atoms and p is zero, one or two;
or a pharmaceutically acceptable salt thereof.

2. A compound of claim 1 wherein X is oxygen.

3. A compound of claim 2 wherein $R_1$, $R_2$ and $R_3$ are selected from a straight or branched alkyl group having from 1 to 6 carbon atoms or a straight or branched alkoxy group having from 1 to 6 carbon atoms.

4. A compound of claim 3 selected from
N-[2,6-bis(1-methylethyl)phenyl]-N'-2-acetyl-5-undecyl-2H-1,2,4-triazol-3-yl)urea,
N-[2,6-bis(1-methylethyl)phenyl]-N'-(5-undecyl-1H-1,2,4-triazol-3-yl)urea,
N-[2,6-bis(1-methylethyl)phenyl]-N'-(2-acetyl-5-dodecyl-2H-1,2,4-triazol-3-yl)urea,
N-[2,6-bis(1-methylethyl)phenyl]-N'-(5-dodecyl-1H-1,2,4-triazol-3-yl)urea,
N-[2,6-bis(1-methylethyl)phenyl]-N'-(2-acetyl-5-tetradecyl-2H-1,2,4-triazol-3-yl)urea,
N-[2,6-bis(1-methylethyl)phenyl]-N'-(5-tetradecyl)-1H-1,2,4-triazol-3-yl)urea,
N-[2,6-bis(1-methylethyl)phenyl]-N'-(2-undecyl-2H-1,2,4-triazol-3-yl)urea,
N-[2,6-bis(1-methylethyl)phenyl]-N-(1-undecyl-1,2,4-triazol-3-yl)urea,
N-[2,6-bis(1-methylethyl)phenyl]-N'-(4-undecyl-1,2,4-triazol-3-yl)urea,
N-[2,6-bis(1-methylethyl)phenyl]N'-(2-dodecyl-1H-1,2,4-triazol-5-yl)urea,
N-[2,6-bis(1-methylethyl)phenyl]-N'-(1-dodecyl-1H-1,2,4-triazol-3-yl)urea,
N-[2,6-bis(1-methylethyl)phenyl]-N'-(4-dodecyl-4H-1,2,4-triazol-3-yl)urea,
4-acetyl-N-[[[2,6-bis(1-methylethyl)phenyl]amino]carbonyl]-5-(dodecyl-thio)-4H-1,2,4-triazol-3-amine,
4-acetyl N-[[[2,6-bis(1-methylethyl)phenyl]amino]carbonyl]-5-(tridecylthio)-4H-1,2,4-triazol-3 amine,
N-[[[2,6-bis(1-methylethyl)phenyl]amino]carbonyl]-5-(tridecylthio)-4H-1,2,4-triazol-3-amine,
N-[2,6-bis(1-methylethyl)phenyl]-N'-[5-(tridecylsulfinyl)-1H-1,2,4-triazol-3-yl]urea,
N-[2,6-bis(1-methylethyl)phenyl]-N'-[5-tridecylsulfonyl)-1H-1,2,4-triazol-3-yl]urea, and
N-[2,6-bis(1-methylethyl)phenyl]amino]carbonyl]-5-(methylthio)-4H 1,2,4-triazol-3-amine.

5. A pharmaceutical composition comprising a compound of claim 1 and a pharmaceutically acceptable carrier.

6. A method of treating hypercholesterolemia and atherosclerosis in a patient in need thereof which comprises administering to said patient an effective amount of a compound of claim 1 together with a pharmaceutically acceptable carrier.

7. A compound of claim 4 selected from
N-[2,6-bis(1-methylethyl)phenyl]-N'-2-acetyl-5-undecyl-2H-1,2,4-triazol-3-yl)urea,
N-[2,6-bis(1-methylethyl)phenyl]-N'-(2-acetyl-5-undecyl-2H-1,2,4-triazol-3-yl)urea,
N-[2,6-bis(2-methylethyl)phenyl]-N'-(5-undecyl-1H-1,2,4-triazol-3-yl)urea,
N-[2,6-bis(1-methylethyl)phenyl)-N'-(2-undecyl-2H-1,2,4-triazol-3-yl)urea,
N-[2,6-bis(2-methylethyl)-phenyl]-N'-(2-undecyl-2H-1,2,4-triazol-3-yl)urea,
N-[2,6-bis(1-methylethyl)-phenyl]-N'-(1-undecyl-1,2,4-triazol-3-yl)urea,
N-[2,6-bis(1-methylethyl)-phenyl]-N'-(2-dodecyl-1H-1,2,4-triazol-5-yl)urea, and
N-[2,6-bis(1-methylethyl)-phenyl]-N'-(1-dodecyl-1H-1,2,4-triazol-3-yl)urea.

* * * * *

UNITED STATES PATENT AND TRADEMARK OFFICE
CERTIFICATE OF CORRECTION

PATENT NO. : 5,185,358
DATED : February 9, 1993
INVENTOR(S) : Creswell et al

It is certified that error appears in the above-indentified patent and that said Letters Patent is hereby corrected as shown below:

Column 22, line 57, insert -- - -- after "4-acetyl"

Column 22, line 67, insert -- - -- after "-4H"

Column 24, line 1, delete "N-[2,6-bis(2" and insert instead -- N-[2,6-bis(1 --

Column 24, line 5, delete "N-[2,6-bis(2" and insert instead -- N-[2,6-bis(1 --

Signed and Sealed this

Eighth Day of February, 1994

Attest:

BRUCE LEHMAN

Attesting Officer

Commissioner of Patents and Trademarks